United States Patent [19]

Jakobson et al.

[11] Patent Number: 5,403,941
[45] Date of Patent: Apr. 4, 1995

[54] PREPARATION OF FATTY ACID ESTERS OF ISOPROPYLIDENE DERIVATIVES OF POLYGLYCEROL

[75] Inventors: Gerald Jakobson; Werner Siemanowski, both of Rheinberg, Germany

[73] Assignee: Deutsche Solvay-Werke GmbH, Solingen, Germany

[21] Appl. No.: 45,091

[22] Filed: Apr. 12, 1993

Related U.S. Application Data

[63] Continuation of Ser. No. 704,391, May 23, 1991, abandoned.

[30] Foreign Application Priority Data

Jun. 7, 1990 [DE] Germany ............ 40 18 220.7

[51] Int. Cl.$^6$ .................................. C07D 317/24
[52] U.S. Cl. ........................ 549/448; 549/454
[58] Field of Search ............... 549/454, 448

[56] References Cited

U.S. PATENT DOCUMENTS 5,024,787  6/1991  Jakobson ................ 549/448

FOREIGN PATENT DOCUMENTS 9904  4/1980  European Pat. Off. .
344419  12/1989  European Pat. Off. .
380411  8/1990  European Pat. Off. .

*Primary Examiner*—Nicky Chan
*Attorney, Agent, or Firm*—Foley & Lardner

[57] ABSTRACT

A process for the preparation of mono-fatty acid or hydroxymono-fatty acid esters of isopropylidene derivatives of a polyglycerol is disclosed. A C6-C22 fatty acid or -hydroxy fatty acid is reacted with isopropylideneglycerol glycidyl ether or diisopropylidenetriglycerol glycidyl ether in a molar ratio of 0.5:1 to 1:0.5 at temperatures of 373473 K. in the presence of a catalyst. The monoisopropylidenediglycerol monofatty acid ester or monoisopropylidenediglycerol hydroxy mono-fatty acid ester or diisopropylidenetetraglycerol mono-fatty acid ester or diisopropylidenetetraglycerol hydroxy mono-fatty acid ester obtained is optionally purified by distillation, fractional distillation and/or ion exchange.

10 Claims, No Drawings

PREPARATION OF FATTY ACID ESTERS OF ISOPROPYLIDENE DERIVATIVES OF POLYGLYCEROL

This application is a continuation, of application Ser. No. 07/704,391, filed May 23, 1991, now abandoned.

BACKGROUND OF THE INVENTION

The present invention relates to a process for the preparation of mono-fatty acid or hydroxy mono-fatty acid esters of isopropylidene derivatives of a polyglycerol.

A process for the preparation of fatty acid or hydroxy fatty acid esters of isopropylidene derivatives of a polyglycerol by reaction of fatty acid alkyl esters or mono- or polyhydroxy fatty acid alkyl esters with one or more isopropylidene derivatives of a polyglycerol is described in German Offenlegungsschrift 3,818,292. In this process, a high outlay in terms of apparatus is necessary for the reaction procedure as, on the one hand, the reaction is carried out in vacuo and, on the other hand, several subsequent distillation steps are necessary for removing and separating the reaction products, since the reaction of the starting substances leads to a mixture of mono- and di-fatty acid esters of the isopropylidene derivatives employed.

SUMMARY OF THE INVENTION

It is therefore an object of the present invention to provide an improved process for the preparation of monofatty acid or hydroxy fatty acid esters of isopropylidene derivatives of a polyglycerol, which can be carried out at normal pressure and which leads to a reaction of the starting substances that is as complete as possible, in which monofatty acid or hydroxy mono-fatty acid esters are exclusively formed, so that a removal and separation of the reaction products which requires an expensive apparatus is not necessary.

These and other objects according to the invention are achieved by a process for the preparation of mono-fatty acid or hydroxy mono-fatty acid esters of isopropylidene derivatives of a polyglycerol, which comprises reacting a C6–C22-fatty acid or -hydroxy fatty acid with isopropylideneglycerol glycidyl ether or diisopropylidenetriglycerol glycidyl ether in a molar ratio of about 0.5:1 to 1:0.5, at temperatures of about 373–473 K., in the presence of a catalyst.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

According to the invention a C6–22-fatty acid or -hydroxy fatty acid is reacted with isopropylideneglycerol glycidyl ether or diisopropylidenetriglycerol glycidyl ether, the starting substances being employed in a molar ratio of 0.5:1 to 1:0.5. The reaction is carried out in the presence of a catalyst at temperatures of about 373–473 K., preferably of about 403–443 K., and the monoisopropylidenediglycerol mono-fatty acid ester or monoisopropylidenediglycerol hydroxy monofatty acid ester or diisopropylidenetetraglycerol monofatty acid ester or diisopropylidenetetraglycerol hydroxy monofatty acid ester obtained is optionally purified by distillation, fractional distillation and/or ion exchange.

The reaction is carried out at normal pressure and, by the process according to the invention, leads exclusively to the mono-fatty acid or hydroxy mono-fatty acid ester in a yield of greater than 95%.

If the reaction is carried out below 100° C., the reaction rates are not sufficiently high, while at temperatures above 200° C. a higher percentage of undesired by-products occurs.

Saturated or unsaturated, branched or unbranched C6–C22 fatty acids, such as, for example, esters of first runnings C6–C10 fatty acids or behenic acid, but preferably C8–C18 fatty acids such as, for example, lauric acid, myristic acid, coconut fatty acids, stearic acid, 2-ethylhexanoic acid, isostearic acid, palm oil fatty acids, oleic acid, soya bean oil fatty acids and/or linoleic acid are employed as fatty acids or hydroxy fatty acids. 12-Hydroxystearic acid or ricinoleic acid are examples, of C8–C18-hydroxy fatty acids.

At least one ammonium salt, one phosphonium salt and/or one tertiary amine, preferably quaternary ammonium or phosphonium salts such as tetrabutylammonium bromide, tetraethylammonium bromide, tetrabutylphosphonium bromide, tetraethylphosphonium bromide and/or 1,6-bis(dimethylamino)hexane is added as the catalyst.

According to a preferred embodiment of the process according to the invention, the catalyst is added in an amount of 0.01–5% by weight, preferably of 0.1–2.5% by weight, relative to the total amount of the compounds to be reacted.

The reaction of the starting substances is expediently carried out in the anhydrous state in order to exclude certain side reactions.

According to a preferred embodiment of the process according to the invention, the reaction of the fatty acid or the hydroxy fatty acid with isopropylideneglycerol glycidyl ether or diisopropylidenetriglycerol glycidyl ether is carried out in a molar ratio of 1:1, by means of which a nearly complete reaction of the starting substances is achieved.

According to a further preferred embodiment, after the reaction of the fatty acid or hydroxy fatty acid with isopropylideneglycerol glycidyl ether or diisopropylidenetriglycerol glycidyl ether, the catalyst is removed by distillation of the reaction mixture.

According to another preferred embodiment, after the reaction of the starting substances, the excess of unreacted fatty acid or hydroxy fatty acid and/or unreacted isopropylideneglycerol glycidyl ether or diisopropylidenetriglycerol glycidyl ether is distilled off in vacuo. A further separation of the remaining reaction product is not necessary.

The monoisopropylidenediglycerol mono-fatty acid esters or monoisopropylidenediglycerol hydroxy mono-fatty acid esters or diisopropylidenetetraglycerol mono-fatty acid esters or diisopropylidenetetraglycerol hydroxy mono-fatty acid esters prepared according to the invention are suitable as intermediates for the preparation of non-ionic surfactants.

They can be employed as solvents or solubilizers for lipid-soluble or oil-soluble active compounds and also in cosmetic preparations.

The following embodiments serve to illustrate the invention, but the invention is not limited to the examples.

Exemplary embodiments

1. Preparation of monoisopropylidenediglycerol monolaurate

Isopropylideneglycerol glycidyl ether (753 g=4 mol) and 2.4 g of tetrabutylammonium bromide are added to a two liter double wall reactor (heating fluid: oil; reaction in an inert gas atmosphere) and the mixture is heated to about 80° C. Lauric acid (800 g=4 mol) is added in portions with stirring. The oil first runnings temperature is then increased to 150° C. If the temperature of the reaction solution reaches about 140° C., the oil first runnings temperature is reduced to 140° C. (if the reaction temperature exceeds 160° C., the oil first runnings temperature may have to be reduced further for a short time). The reaction is complete after about 3.5 h (acid number: <10, <2% of unreacted glycidyl ether).

Unreacted starting materials are removed by distillation in vacuo, and the crude product is either employed in further syntheses (for example, protective group removal) or prepared in pure form by molecular distillation.

The amount of monoisopropylidenediglycerol monolaurate obtained is 1.4 kg (about 90% of theory) as a crude product.

2. Preparation of diisopropylidenetetraglycerol monolaurate

Diisopropylidenetriglycerol glycidyl ether (752 g=2 mol) and 3.0 g of tetrabutylammonium bromide are added to a two liter double-wall reactor (heating fluid: oil; reaction in an inert gas atmosphere) and the mixture is heated to about 80° C. Lauric acid (400 g=2 mol) are added in portions with stirring and the oil first runnings temperature is then increased to 160° C. The reaction time is complete after about 3.5 h (acid number <10, <2% of unreacted glycidyl ether).

Unreacted starting materials are removed by molecular distillation, and the crude product is either employed in further syntheses (for example, protective group removal) or prepared in pure form by molecular distillation. The amount of diisopropylidenetetraglycerol monolaurate obtained is 980 g (about 85% of theory) as a crude product.

What is claimed is:

1. A process for the preparation of mono-fatty acid or hydroxy mono-fatty acid esters of isopropylidene derivatives of a polyglycerol, which comprises reacting a C6-C22-fatty acid or -hydroxy fatty acid with isopropylideneglycerol glycidyl ether or diisopropylidenetriglycerol glycidyl ether in a molar ratio of about 0.5:1 to 1:0.5, at temperatures of about 373°–473° K. in the presence of a catalyst selected from the group consisting of a quaternary ammonium salt, a quaternary phosphonium salt and 1,6-bis(dimethylamino)hexane.

2. The process as claimed in claim 1, additionally comprising the step of purifying the monoisopropylidenediglycerol mono-fatty acid ester or monoisopropylidenediglycerol hydroxy mono-fatty acid ester, diisopropylidenetetraglycerol mono-fatty acid ester or diisopropylidenetetraglycerol hydroxy mono-fatty acid ester by at least one of distillation, fractional distillation and ion exchange.

3. The process as claimed in claim 1, wherein the catalyst is selected from the group consisting of tetrabutylammonium bromide, tetraethylammonium bromide, tetrabutylphosphonium bromide, tetraethylphosphonium bromide and 1,6-bis(bis(dimethylamino)hexane.

4. The process as claimed in claim 1, wherein the catalyst is added in an amount of 0.01–5% by weight, relative to the total amount of the compounds to be reacted.

5. The process as claimed in claim 1, wherein a C8–C18-fatty acid or -hydroxy fatty acid is reacted.

6. The process as claimed in claim 1, wherein, after the reaction of the fatty acid or hydroxy fatty acid with isopropylideneglycerol glycidyl ether or diisopropylidenetriglycerol glycidyl ether, the catalyst is removed by distillation of the reaction mixture.

7. The process as claimed in claim 1, wherein, after the reaction of the fatty acid or hydroxy fatty acid with isopropylideneglycerol glycidyl ether or diisopropylidenetriglycerol glycidyl ether, the excess of the unreacted fatty acid or hydroxy fatty acid and the unreacted isopropylideneglycerol glycidyl ether or diisopropylidenetriglycerol glycidyl ether is distilled off in vacuo.

8. The process as claimed in claim 1, wherein the ratio of fatty acid to ether is about 1.

9. The process as claimed in claim 1, wherein the temperature is about 403–443 K.

10. The process as claimed in claim 1, wherein the amount of catalyst added is about 0.1 to 2.5% by weight.

* * * * *